US010716896B2

(12) United States Patent
O'Connor et al.

(10) Patent No.: US 10,716,896 B2
(45) Date of Patent: Jul. 21, 2020

(54) WEARABLE AUTOMATED MEDICATION DELIVERY SYSTEM

(71) Applicant: INSULET CORPORATION, Acton, MA (US)

(72) Inventors: Jason O'Connor, Acton, MA (US); Daniel Allis, Boxford, MA (US); David Nazzaro, Groveland, MA (US); John R. Bussiere, Littleton, MA (US); John D'Arco, Wilmington, MA (US)

(73) Assignee: INSULET CORPORATION, Acton, MA (US)

( * ) Notice: Subject to any disclaimer, the term of this patent is extended or adjusted under 35 U.S.C. 154(b) by 318 days.

(21) Appl. No.: 15/359,187

(22) Filed: Nov. 22, 2016

(65) Prior Publication Data

US 2017/0173261 A1    Jun. 22, 2017

Related U.S. Application Data

(60) Provisional application No. 62/290,577, filed on Feb. 3, 2016, provisional application No. 62/259,143, filed on Nov. 24, 2015.

(51) Int. Cl.
*A61M 5/172* (2006.01)
*G16H 40/63* (2018.01)
(Continued)

(52) U.S. Cl.
CPC ...... *A61M 5/1723* (2013.01); *A61M 5/14248* (2013.01); *G06F 19/3468* (2013.01);
(Continued)

(58) Field of Classification Search
CPC ............ A61M 5/1723; A61M 5/14248; A61M 2230/201; G16H 20/17; G16H 20/10; G06F 19/3468
See application file for complete search history.

(56) References Cited

U.S. PATENT DOCUMENTS

| 4,067,000 A | 1/1978 | Carlson |
| 4,211,998 A | 7/1980 | Junginger et al. |

(Continued)

FOREIGN PATENT DOCUMENTS

| DE | 19920896 A1 | 11/2000 |
| WO | 0029047 A1 | 5/2000 |

(Continued)

OTHER PUBLICATIONS

International Search Report; PCT/US16/63420; dated Mar. 29, 2017.

*Primary Examiner* — Kami A Bosworth
*Assistant Examiner* — Leah J Swanson (57) ABSTRACT

Systems and methods for automatically delivering medication to a user. A sensor coupled to a user can collect information regarding the user. A controller can use the collected information to determine an amount of medication to provide the user. The controller can instruct a drug delivery device to dispense the medication to the user. The drug delivery device can be a wearable insulin pump that is directly coupled to the user. The controller can be part of or implemented in a cellphone. A user can be required to provide a confirmation input to allow a determined amount of insulin to be provided to the user based on detected glucose levels of the user. The sensor, controller, and drug delivery device can communicate wirelessly.

16 Claims, 6 Drawing Sheets

(51) Int. Cl.
*G16H 20/17* (2018.01)
*A61M 5/142* (2006.01)
*G06F 19/00* (2018.01)

(52) U.S. Cl.
CPC .............. *G16H 20/17* (2018.01); *G16H 40/63* (2018.01); *A61M 2205/27* (2013.01); *A61M 2205/3569* (2013.01); *A61M 2205/3584* (2013.01); *A61M 2205/581* (2013.01); *A61M 2205/582* (2013.01); *A61M 2205/583* (2013.01); *A61M 2205/8206* (2013.01); *A61M 2230/201* (2013.01)

(56) References Cited

U.S. PATENT DOCUMENTS

| | | | |
|---|---|---|---|
| 4,231,019 A | 10/1980 | Junginger et al. | |
| 4,514,732 A | 4/1985 | Hayes, Jr. | |
| 4,855,746 A | 8/1989 | Stacy | |
| 4,871,351 A | 10/1989 | Feingold | |
| 5,551,953 A | 9/1996 | Lattin et al. | |
| 5,569,187 A | 10/1996 | Kaiser | |
| 5,630,710 A | 5/1997 | Tune et al. | |
| 5,764,159 A | 6/1998 | Neftel | |
| 5,845,218 A | 12/1998 | Altschul | |
| 5,875,393 A | 2/1999 | Altschul et al. | |
| 5,886,647 A | 3/1999 | Badger et al. | |
| 5,983,094 A | 11/1999 | Altschul et al. | |
| 6,061,580 A | 5/2000 | Altschul et al. | |
| 6,144,847 A | 11/2000 | Altschul et al. | |
| 6,427,088 B1 | 7/2002 | Bowman, IV et al. | |
| 6,554,798 B1 | 4/2003 | Mann et al. | |
| 6,558,320 B1 | 5/2003 | Causey, III et al. | |
| 6,572,585 B2 | 6/2003 | Choi | |
| 6,645,142 B2 | 11/2003 | Braig et al. | |
| 6,656,159 B2 | 12/2003 | Flaherty | |
| 6,669,669 B2 | 12/2003 | Flaherty et al. | |
| 6,689,091 B2 | 2/2004 | Bui et al. | |
| 6,692,457 B2 | 2/2004 | Flaherty | |
| 6,749,587 B2 | 6/2004 | Flaherty | |
| 6,768,425 B2 | 7/2004 | Flaherty et al. | |
| 6,960,192 B1 | 11/2005 | Flaherty et al. | |
| 7,029,455 B2 | 4/2006 | Flaherty | |
| 7,137,964 B2 | 11/2006 | Flaherty | |
| 7,887,505 B2 | 2/2011 | Flaherty | |
| 8,140,275 B2 | 3/2012 | Campbell et al. | |
| 8,622,954 B2 * | 1/2014 | Shahmirian | A61M 5/14276 604/66 |
| 8,663,103 B2 * | 3/2014 | Causey, III | A61B 5/0002 600/300 |
| 2002/0040208 A1 | 4/2002 | Flaherty et al. | |
| 2002/0065454 A1 | 5/2002 | Lebel et al. | |
| 2002/0107476 A1 | 8/2002 | Mann et al. | |
| 2002/0126036 A1 | 9/2002 | Flaherty et al. | |
| 2003/0055406 A1 | 3/2003 | Lebel et al. | |
| 2003/0088238 A1 * | 5/2003 | Poulsen | A61M 5/1413 604/890.1 |
| 2003/0212379 A1 | 11/2003 | Bylund et al. | |
| 2004/0010207 A1 | 1/2004 | Flaherty et al. | |
| 2005/0171512 A1 | 8/2005 | Flaherty | |
| 2006/0282290 A1 | 12/2006 | Flaherty et al. | |
| 2007/0112298 A1 | 5/2007 | Mueller et al. | |
| 2011/0118578 A1 | 5/2011 | Timmerman et al. | |
| 2011/0257496 A1 | 10/2011 | Terashima et al. | |
| 2012/0277667 A1 | 11/2012 | Yodat et al. | |
| 2014/0039383 A1 | 2/2014 | Dobbles et al. | |
| 2014/0148779 A1 | 5/2014 | Rao et al. | |
| 2014/0309615 A1 * | 10/2014 | Mazlish | A61B 5/14532 604/504 |
| 2015/0164390 A1 * | 6/2015 | Larvenz | A61B 5/14532 600/365 |
| 2015/0173674 A1 * | 6/2015 | Hayes | A61B 5/681 600/301 |
| 2015/0217052 A1 | 8/2015 | Keenan et al. | |

FOREIGN PATENT DOCUMENTS

| | | |
|---|---|---|
| WO | 0152727 A1 | 7/2001 |
| WO | 0220073 A2 | 3/2002 |
| WO | 2003090509 A3 | 4/2003 |

* cited by examiner

WEARABLE AUTOMATED MEDICATION DELIVERY SYSTEM

CROSS-REFERENCE TO RELATED APPLICATIONS

This application claims priority to U.S. Provisional Patent Application No. 62/259,143, filed Nov. 24, 2015, and to U.S. Provisional Patent Application No. 62/290,577, filed Feb. 3, 2016, the entirety of which are hereby incorporated by reference.

TECHNICAL FIELD

Embodiments herein generally relate to automated medication delivery and, more particularly, to wireless medication delivery systems using wearable medication delivery devices.

BACKGROUND

Medication delivery systems typically delivery a medication to a user based on health conditions of the user. For example, an "artificial pancreas" (AP) system can monitor a user's glucose levels, determine an appropriate level of insulin for the user based on the monitored glucose levels, and subsequently dispense the insulin to the user. Sophisticated control algorithms needed for AP systems and other medication delivery systems generally require powerful computing resources and significant power resources. As a result, conventional medication delivery systems do not provide for wireless communications between system components, fully autonomous operation, enhanced user experiences involving ubiquitous electronic devices like cellphones, and heightened security features. A need therefore exists for a medication delivery system, such as an insulin management system, that includes such features.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Various embodiments of the present invention include systems and methods for delivering a medication to a person using a wearable medical device in accordance with a wireless signal received from an electronic device. In various embodiments, the electronic device is a smart watch, smart necklace, module attached to the medical device, or any other type or sort of electronic device that may be worn or carried on the body of the person and executes an algorithm that computes the times and dosages of delivery of the medication. For example, the electronic device may execute an artificial-pancreas algorithm that computes the times and dosages of delivery of insulin. The electronic device may also be in communication with a sensor, such as a glucose sensor, that collects data on a physical attribute or condition of the person, such as a glucose level. The sensor may be disposed in or on the body of the person and may be part of the medical device or may be a separate device. Alternately, the medical device may be in communication with the sensor in lieu of or in addition to the communication between the sensor and the electronic device. The communication may be direct (if, e.g., the sensor is integrated with or otherwise a part of the medical device) or remote/wireless (if, e.g., the sensor is disposed in a different housing than the medical device). In these embodiments, the sensor and/or medical device contains computing hardware (e.g., a processor, memory, firmware, etc.) that executes some or all of the algorithm that computes the times and dosages of delivery of the medication.

Various embodiments described herein include systems and methods for automatically delivering medication to a user. A sensor coupled to a user can collect information regarding the user. A controller can use the collected information to determine an amount of medication to provide the user. The controller can instruct a drug delivery device to dispense the medication to the user. The drug delivery device can be a wearable insulin pump that is directly coupled to the user. The controller can be part of or implemented in a cellphone. A user can be required to provide a confirmation input to allow a determined amount of insulin to be provided to the user based on detected glucose levels of the user.

Figure 1A:
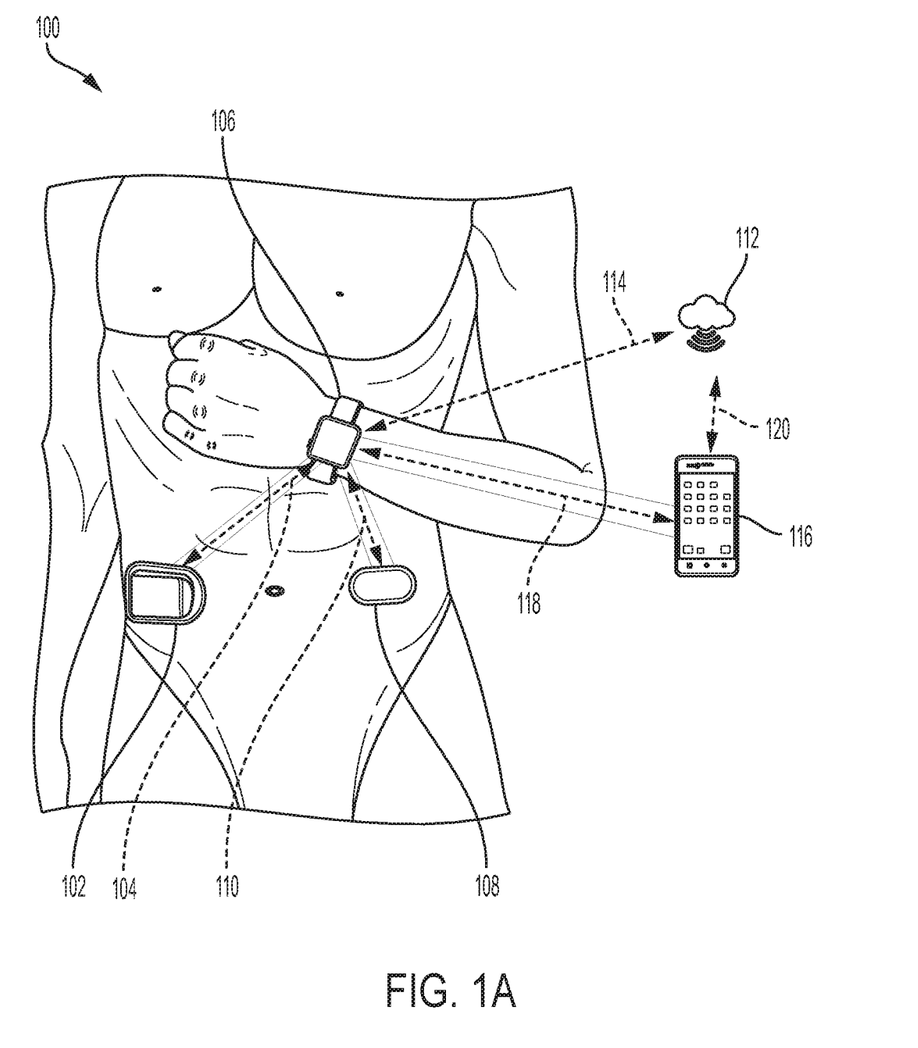
FIG. 1A illustrates a first exemplary wearable automated medication delivery system.

FIG. 1A illustrates a first exemplary wearable automated medication delivery system 100. The wearable automated medication delivery system 100 can include a medical device 102. The medical device 102 can be attached to the body of a user and can deliver a medication to the user. The medical device 102 can be a wearable device. In particular, the medical device 102 can be directly coupled to a user (e.g., directly attached to a body part and/or skin of the user). A surface of the medical device 102 can include an adhesive to facilitate attachment to the user.

The medical device 102 can include a number of components to facilitate automated delivery of a medication to the user. For example, the medical device 102 can include a reservoir for storing the medication, a needle or cannula for delivering the medication into the body of the person, and a pump for transferring the medication from the reservoir, through the needle or cannula, into the body of the user. The medical device 102 can also include a power source such as a battery for supplying power to the pump and/or other components of the medical device 102.

The medical device 102 can store and provide any medication or drug to the user. In various embodiments, the medical device 102 can be an automated wearable insulin delivery device. For example, the medical device 102 can be the OmniPod® (Insulet Corporation, Billerica, Mass.) insulin delivery device as described in U.S. Pat. Nos. 7,303,549, 7,137,964, or U.S. Pat. No. 6,740,059, each of which is incorporated herein by reference in its entirety.

The medical device 102 can also contain analog and/or digital circuitry for controlling the delivery of the medication. The circuitry can be implemented as a controller. The circuitry can include discrete, specialized logic and/or components, an application-specific integrated circuit, a microcontroller or processor that executes software instructions, firmware, or any combination thereof. In various embodiments, the control circuitry can be configured to cause the pump to deliver doses of the medication to the person at predetermined intervals. The size and/or timing of the doses may be programmed into the control circuitry using a wired or wireless link by the user or by a third party (such as a health care provider).

Instructions for determining the delivery of the medication to the user (e.g., the size and/or timing of any doses of the medication) can originate locally (e.g., based on determinations made by the medical device 102) or can originate remotely and then provided to the medical device 102. Remote instructions can be provided to the medical device 102 over a wired or wireless link. The medical device 102 can execute any received instructions for the delivery of the medication to the user. In this way, under either scenario, the delivery of the medication to the user can be automated.

In various embodiments, the medical device 102 can communicate via a wireless link 104 with an electronic device 106. The electronic device 106 can be any electronic device such as, for example, an Apple® Watch. The electronic device 106 can be a wearable wireless accessory device. The wireless link 104 can be any type of wireless link provided by any known wireless standard. As an example, the wireless link can provide communications based on Bluetooth®, Wi-Fi, a near-field communication standard, a cellular standard, or any other wireless protocol.

Figure 1B:
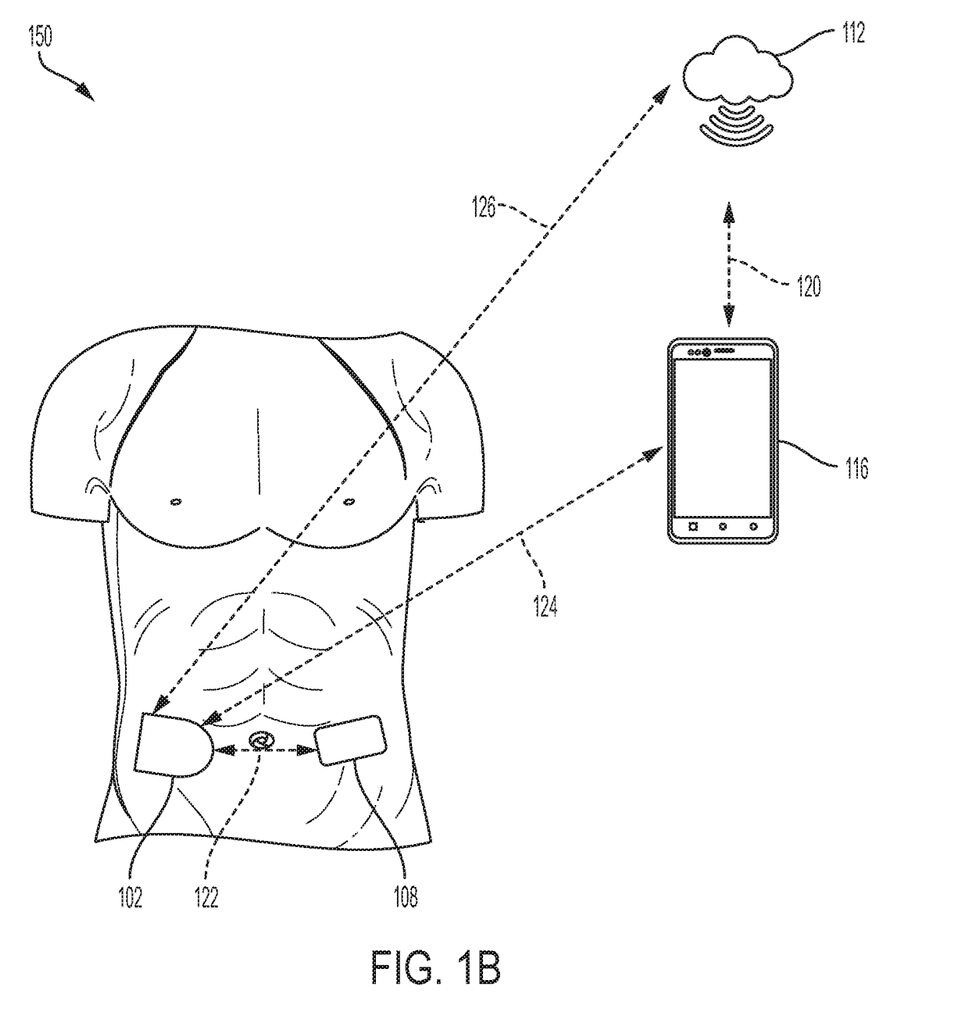
FIG. 1B illustrates a second exemplary wearable automated medication delivery system.

FIG. 1B illustrates a second exemplary wearable automated medication delivery system 150. The wearable automated medication delivery system 150 can also include the medical device 102. As shown in FIG. 1B, the medical device 102 can communicate via a wireless link 122 with a sensor 108. The wireless link 122 can be the same type of communication link as the link 104 in that it can provide wireless communications over any known wireless protocol or standard.

The control circuitry in the medical device 102 may include circuitry implementing a wireless transmitter, receiver, and/or transceiver for communication over the link 104 or 122. Information may be transmitted between the medical device 102 and the electronic device 106 over the link 104 and/or between the medical device 102 and the sensor 108 over the link 122. The shared information may include handshake/pairing information, data, commands, status information, or any other such information.

In various embodiments, the electronic device 106 transmits a command to the medical device 102 that specifies an action for the medical device 102 to take regarding delivery of the medication. In another embodiment, the sensor 108 sends a signal to the medical device 102 via the link 122, and the medical device 102 executes an algorithm to determine an action for the medical device 102 to take regarding delivery of the medication. The action may be delivery of a bolus of the medication, a change in a time, frequency, or schedule of future deliveries of the medication, a change in a size of future deliveries of the medication, or any other such action. The command may further comprise a bolus size, a bolus time, or any other such additional information. The medical device 102 may transmit a confirmation message back to the electronic device 106 upon receipt of the command and/or after completion of the action.

In various embodiments, the electronic device 106 transmits the command as specified by an algorithm executing thereon, such as an artificial-pancreas algorithm. The algorithm may execute in the context of a software application running on the electronic device. The user may download this application from an application store, such as the Apple® iTunes® store, or from any other source. The algorithm may be used to compute appropriate times and doses of delivery of the medication. In some embodiments, the algorithm bases these computations at least in part on information known about the person, such as sex, age, weight, or height, and/or on information gathered about a physical attribute or condition of the person (e.g., from the sensor 108). For example, the algorithm may determine an appropriate delivery of the medication based on glucose level monitoring of the user. The software application may further permit the person to access status information regarding the medical device 102, such as its battery level, number of doses remaining, amount of time in use, or other such status information. The software application may instead or in addition allow the person to issue commands to the medical device 102, such as a command to deliver a bolus.

In various embodiments, as shown in FIGS. 1A and 1B, the sensor 108 is worn on the body of the person or implanted within the person and is used to collect information regarding one or more physical attributes or conditions of the person. The sensor 108 can be coupled to the user and worn on a body part of the user. The sensor 108 can be a glucose sensor. For example, the sensor 108 can be a continuous glucose monitor (CGM). Although the sensor 108 is depicted as separate from the medical device 102, in various embodiments, the sensor 108 and medical device 102 may be incorporated into the same unit. That is, in various embodiments, the sensor 108 can be a part of the medical device 102 and contained within the same housing of the medical device 102 (e.g., the sensor 108 can be positioned within or embedded within the medical device).

The sensor 108 can include one or more sensing elements, an electronic transmitter, receiver, and/or transceiver for communicating with the electronic device 106 over a link 110 or with medical device 102 over the link 122. The link 110 can be the same type of wireless link as the links 104 or 122. The sensor 108 can also include a power source for supplying power to the sensing elements and/or transceiver. Communications provided by the sensor 108 may include data gathered from the sensing elements. This data can be transmitted continually, at periodic intervals, and/or during or after a change in sensed data (e.g., if a glucose level or rate of change in the level exceeds a threshold). The software application executing the algorithm may use this collected information to send a command to the medical device 102 to, for example, deliver a bolus to the person, change the amount or timing of future doses, or other commands.

The electronic device 106 can be considered to be a wireless accessory device or an intermediate device. In various embodiments, the electronic device 106 can relay commands for delivery of a medication from a remote source to the medical device 102. In various embodiments, the electronic device 106 can include a controller for determining delivery of the medication (e.g., the electronic device can include a controller for executing an "artificial pancreas" algorithm). The electronic device 106 can also relay sensor data from the sensor 108 to the medical device 102. In general, the electronic device 106 can relay communications between any of the devices depicted in FIGS. 1A and 1B (e.g., communications in any direction between any two devices depicted).

The sensor 108 can be any type of sensor and is not limited to a CGM. The sensor 108 can include one or more sensors housed in the same physical unit.

The electronic device 106 and/or the medical device 102 may communicate with one more remote devices 112, which may include computers, servers, storage devices, cloud-based services, or other similar devices. The remote device 112 may be owned or operated by, for example, health-care companies or services, pharmacies, doctors, nurses, or other such medically-related entities. The remote device 112 may include a cloud-based data management system. A user may wish, for example, to back up data collected from the sensor 108, back up a record of medication delivery times and doses provided by the medical device 102, or back up other such information. A wireless link 114 may be used to connect the electronic device 106 to the remote devices 112 and/or a wireless link 126 may be used to connect the medical device 102 to the remote devices 112. The wireless links 114 and 126 can be of the same type as the other wireless links described herein.

Alternatively or in addition thereto, the electronic device 106 may communicate with a local device 116. The local device 116 can be a dedicated control or monitoring device (e.g., a diabetes management device and/or a custom hand-held electronic computing device), cellular phone, laptop computer, tablet, desktop computer, or other similar electronic computing device. The local device 116 can communicate with the electronic device 106 over a wireless link 118. The wireless link 118 can be of the same type as the other wireless links described herein.

A software application executing on the local device 116 may be used to send commands to the medical device 102 (e.g., via the electronic device 106) and/or receive status information about the medical device 102 (e.g., via the electronic device 106). In other embodiments, the local device 116 instead or in addition communicates directly via a wireless link 124 with the medical device 102. The wireless link 124 can be of the same type as the other wireless links described herein.

Additionally, the sensor 108 may communicate via a wireless link with the local device 116. The local device 116 may communicate with the remote devices 112 via a wireless link 120. The wireless link 120 can be of the same type as the other wireless links described herein.

Figure 2:
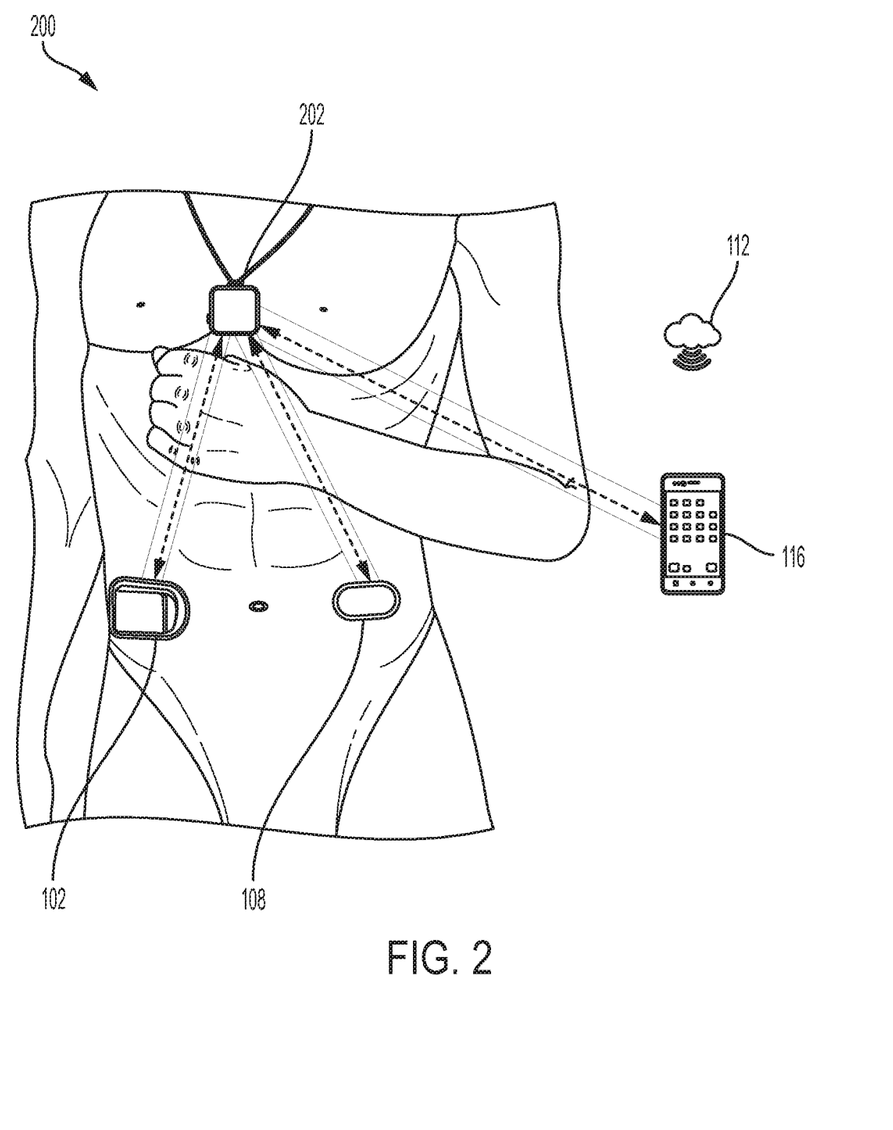
FIG. 2 illustrates a third exemplary wearable automated medication delivery system.

FIG. 2 illustrates a third exemplary wearable automated medication delivery system 200. As part of the wearable automated medication delivery system 200, an electronic device 202 can hang from a necklace or lanyard hung around a user's neck. Alternatively, the electronic device 202 can be a wearable patch. The electronic device 202 can operate and provide the functionality of the electronic device 106. That is, the electronic device 202 can include some or all of the features described above with reference to the electronic device 106 of FIG. 1A Each of the wearable automated medication delivery systems 100, 150, and 200 described in relation to FIGS. 1A, 1B, and 2 can be part of a diabetes management system. Such a diabetes management system can monitor a user's glucose levels (as well as other physical attributes of a person) and can determine appropriate levels of insulin to provide a user over time. The appropriate levels of insulin (e.g., in terms of dosages and delivery times) can be adjusted over time based on the user's glucose levels or other physical conditions. The insulin to provide a user can be determined using an "artificial pancreas" algorithm. The algorithm can be implemented by a controller that executes instructions stored in a memory. The controller can determine the amount of insulin to provide based on received sensor data (e.g., glucose levels of the user). The controller can then instruct the medical device 102 of the automated medication delivery systems 100, 150, and 200 to automatically deliver the determined amount of insulin to a user.

The controller for determining the delivery of insulin to the user, any sensor used for collecting and providing data to the controller, and any device providing monitoring output information and capable of receiving user input information can be distributed in any manner across any number of devices. In various embodiments, a glucose sensor (e.g., the sensor 108) is provided as a separate device from a wearable insulin pump (e.g., the medical device 102). In various embodiments, a glucose sensor (e.g., the sensor 108) is provided as part of a wearable insulin pump (e.g., the medical device 102). In various embodiments, the controller for determining the delivery of insulin to the user (e.g., the controller for executing the "artificial pancreas" algorithm) can be provided within a wearable insulin pump (e.g., the medical device 102). In various embodiments, the controller for determining the delivery of insulin to the user (e.g., the controller for executing the "artificial pancreas" algorithm) can be provided in a separate electronic device (e.g., the electronic device 106, the electronic device 202, the local device 116, or the remote device 112).

In various embodiments, any device or component forming a part of a diabetes management systems provided by the wearable automated medication delivery systems 100, 150, and 200 can communicate wirelessly with any other device or component of the system. Any type of wireless link can be used based on any known wireless standard or protocol. Further, in various embodiments, one or more of the devices or components can communicate with one or more remote severs or computing devices including remote cloud-based server systems to provide further monitoring, backup, storage, and/or processing capabilities. The components shown in the wearable automated medication delivery systems 100, 150, and 200 can communicate directly with one another or can communicate indirectly using a relay or intermediate communication device such as, for example, the electronic device 106 or 202.

In various embodiments, the controller for determining the delivery of insulin to the user (e.g., for executing an "artificial pancreas" algorithm) can be provided as part of an electronic device (e.g., the electronic device 106 or electronic device 202) that is separate from a sensor (e.g., the sensor 108) for monitoring a condition or attribute of the user and separate from a wearable insulin pump (e.g., the medical device 102). Under such a scenario, the sensor 108 can send sensor data (e.g., glucose level data or other user data) to the electronic device 106 or 202. The electronic device 106 or 202 can determine an insulin dose based on the received sensor data. The electronic device 106 or 202 can then communicate the determined dosage to the wearable insulin pump 102. The wearable insulin pump 102 can then automatically provide the dosage to the user without patient input. Monitoring data (e.g., glucose level data and/or dosage data) can be provided to a monitoring device (e.g., the local device 116 or a remote device 112) for storage or review (e.g., presentation of current or past data related to delivery of the insulin to the user).

In various embodiments, the controller for determining the delivery of insulin to the user (e.g., for executing an "artificial pancreas" algorithm) can be provided as part of the wearable insulin pump (e.g., the medical device 102). Under such a scenario, the sensor 108 can send sensor data (e.g., glucose level data or other user data) to the wearable insulin pump 102. The wearable insulin pump 102 can determine an insulin dose based on the received sensor data. The wearable insulin pump 102 can then automatically provide the dosage to the user without patient input. Monitoring data (e.g., glucose level data and/or dosage data) can be provided to a monitoring device (e.g., the local device 116 or a remote device 112) for storage or review (e.g., presentation of current or past data related to delivery of the insulin to the user). Under this scenario, the wearable insulin pump 102 (which can operate as a drug delivery device) can include a communications interface built-in to the wearable insulin pump 102 to provide wireless communication capabilities. Alternatively, an add-on device can be coupled to the wearable insulin pump 102 (e.g., an attachable device) to provide a wireless communication interface and wireless communication capabilities to the wearable insulin pump 102.

In various embodiments, the controller for determining the delivery of insulin to the user (e.g., for executing an "artificial pancreas" algorithm) can be provided as part of the wearable insulin pump (e.g., the medical device 102). Further, the sensor 108 can be provided as part of the wearable insulin pump 102. That is, the sensor 108 can be embedded within the wearable insulin pump 102. Under such a scenario, the sensor 108 can send sensor data (e.g., glucose level data or other user data) to the wearable insulin pump 102. The wearable insulin pump 102 can determine an insulin dose based on the received sensor data. The wearable insulin pump 102 can then automatically provide the dosage to the user without patient input. Monitoring data (e.g., glucose level data and/or dosage data) can be provided to a monitoring device (e.g., the local device 116 or a remote device 112) for storage or review (e.g., presentation of current or past data related to delivery of the insulin to the user).

In various embodiments, the controller for determining the delivery of insulin to the user (e.g., for executing an "artificial pancreas" algorithm) can be provided as part of the local electronic device 116. For example, the local electronic device 116 can be a mobile device or a cellphone. The cellphone 116 can include an app for determining insulin delivery to the user. Under such a scenario, the sensor 108 can send sensor data (e.g., glucose level data or other user data) to the cellphone 116 (e.g., directly or indirectly using the electronic device 106 or 202 as a relay). The cellphone 116 can determine an insulin dose based on the received sensor data. The cellphone 116 can communicate the insulin dosage information to the wearable insulin pump 102. The cellphone 116 can communicate with the wearable insulin pump 102 directly or indirectly—for example, indirectly by way of the electronic device 106 or 202. After receiving the dosage information, the wearable insulin pump 102 can provide the dosage to the user. Monitoring data (e.g., glucose level data and/or dosage data) can be provided to a monitoring device (e.g., the local device 116 or a remote device 112) for storage or review (e.g., presentation of current or past data related to delivery of the insulin to the user). As an alternative to a cellphone, the local device 116 can be a dedicated handheld electronic computing device that does not include all of the capabilities of a cellphone (e.g., does not provide an Internet connection or cellular communications interface).

When dosage information is generated and/or provided from the cellphone 116, user input can be required before the wearable insulin pump 102 is allowed to provide the dosage. For example, a user may be required to confirm a command to provide a dosage before the dosage is provided. The wearable insulin pump 102 or the electronic device 106 can include an output device for alerting the user that user confirmation is requested. The alert can be an alarm or notification provided visually, audibly, or by other means (e.g., such as vibrating). The wearable insulin pump 102 or the electronic device 106 can further include a user input device for receiving a confirmation input from the user. For example, the user input can be provided by tapping or pressing a button or by receiving an input using an accelerometer provided on the wearable insulin pump 102 or the electronic device 106. This confirmation requirement can represent a cybersecurity measure for the safety of the user.

In various embodiments, the user can be required to provide a confirmation input within a predetermined amount of time after the alarm or notification is provided. If the confirmation is not received within the predetermined amount of time, then the delivery of the insulin to the user can be blocked. Alternatively, if the confirmation is received within the predetermined amount of time, then delivery can be provided as planned. The alarm or alert can indicate receipt of an instruction relating to delivery of the insulin to the user. The confirmation can protect the user from erroneously scheduled insulin delivery to the user. In various embodiments, when a dedicated handheld electronic device is used rather than a cellphone for the local device, such confirmation requirements may not be implemented as the security risk to the user is reduced.

In various embodiments, the electronic device 106 can be provided to include the controller for determining medication dosages and times and/or for providing communications between one or more other components of the systems 100, 150, and 200. In various other embodiments, the electronic device 106 is not necessarily present when the controller for determining medication dosages and times can be housed in another component of the systems 100, 150, and 200 and/or when the other system components can communicate without using the electronic device 106 as an intermediary.

Figure 3A:
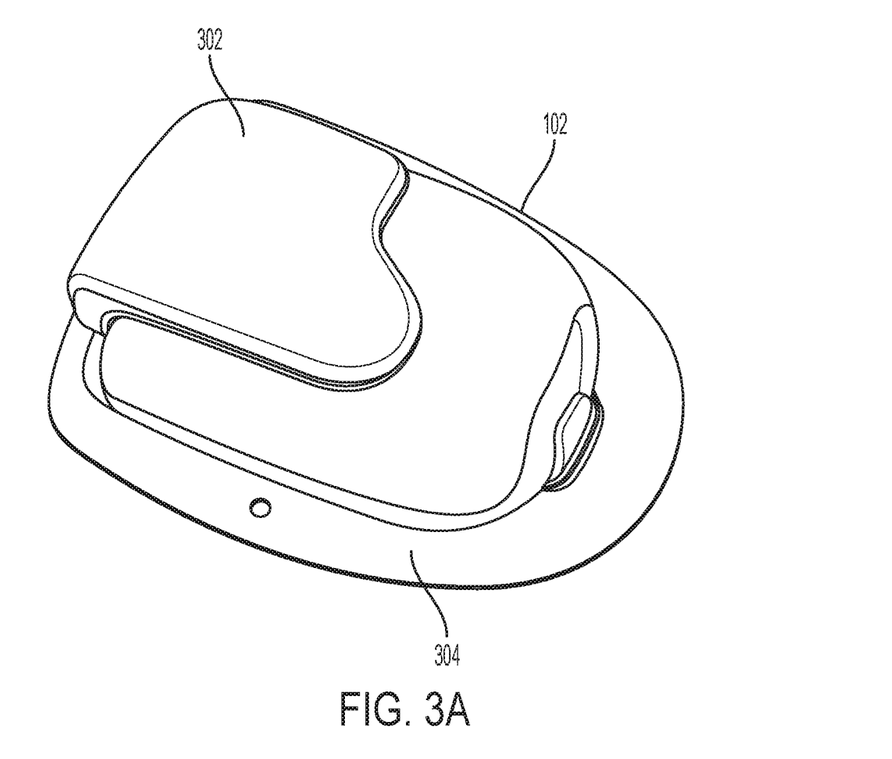
FIGS. 3A and 3B illustrate first and second views of a medical device depicted in FIGS. 1A, 1B, and 2.
Figure 3B:
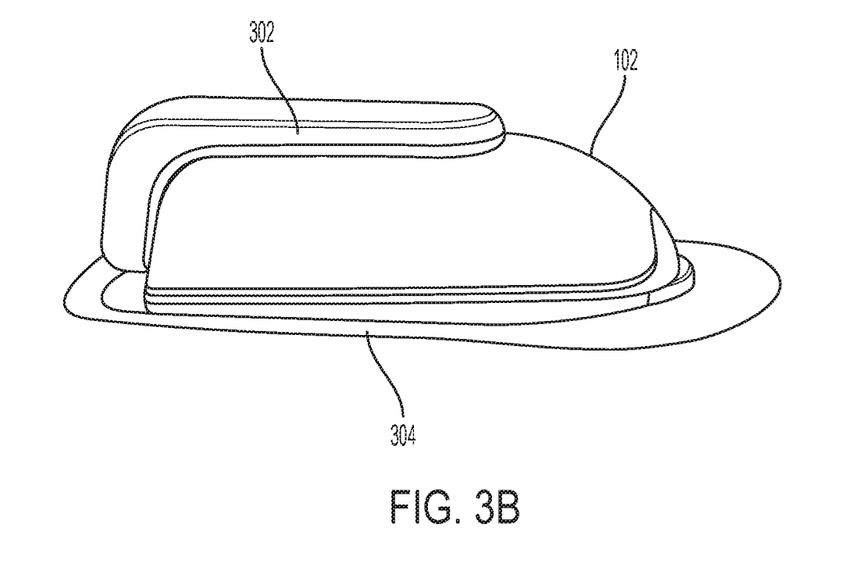

FIGS. 3A and 3B illustrate first and second views of the medical device 102. As shown in FIGS. 3A and 3B, the medical device 102 can include an electronics module 302 that is attached or coupled to the medical device 102. Further, the medical device 102 can include a pad or other surface 304 for adhering to the user. The pad 304 can be coupled to a portion of the medical device 102. The pad 304 can include an adhesive that can be used to attach the medical device 102 to the user.

The attached module 302 can include some or all of the features described above with reference to the electronic device 106 of FIG. 1A. In various embodiments, the module 302 can include a transceiver to enable the medical device 102 to wirelessly communicate with any other device or component depicted in FIG. 1A, 1B, or 2. The module 302 and the medical device 102 can communicate over any known wireless or wired communication standard or protocol. In some embodiments, for example, near-field communication is used for communication between the medical device 102 and the module 302. In other embodiments, a wired connection, such as a universal serial bus connection, is used for communication between the medical device 102 and the module 302.

The electronics module 302 may be removably attached to the medical device 102 so that the electronics module 302 may be used with a plurality of medical devices 102. The electronics module 302 may be sealed and waterproof. The electronics module 302 may have a battery that can be rechargeable using wireless charging.

In various embodiments, the medical device 102 described herein includes a user-input device and/or a user-output device. The user-input device can be a button disposed on the device 102, an acceleration sensor for sensing motion of the medical device 102, or any other such input device. The user-output device may be a speaker for playing sound, a vibration generator (e.g., a motorized gear with an offset center of gravity) for creating vibrations, metal terminals for delivering an electric shock to the body of the person, a visual display and/or one or more lights for providing a visual alarm, or any other such output device.

In various embodiments, when a command is received at the medical device 102 from the electronic device 106, the electronic device 202, or from the local electronic device 116, an action associated with the command (e.g., delivery of a bolus) is not carried out until input is received from the user. The input may include pressing the button on the medical device 102, shaking the medical device 102 (as sensed by the acceleration sensor), tapping the medical device 102 one or more times (as sensed by the acceleration sensor), scanning an RFID or NFC tag, keycard, or fob, or any other such input. If an input is not received within a certain amount of time (e.g., 30 seconds, one minute, two minutes, or any other amount of time), the medical device 102 may not carry out the action. That is, a determined insulin dose may not be delivered. In some embodiments, the output device alerts the person to the arrival of the command at the medical device 102 by, for example, sounding an alarm, vibrating, or providing a visual signal or other notification. The output device may similarly alert the user after execution of the action and/or if the action is cancelled due to lack of user input.

Figure 4:
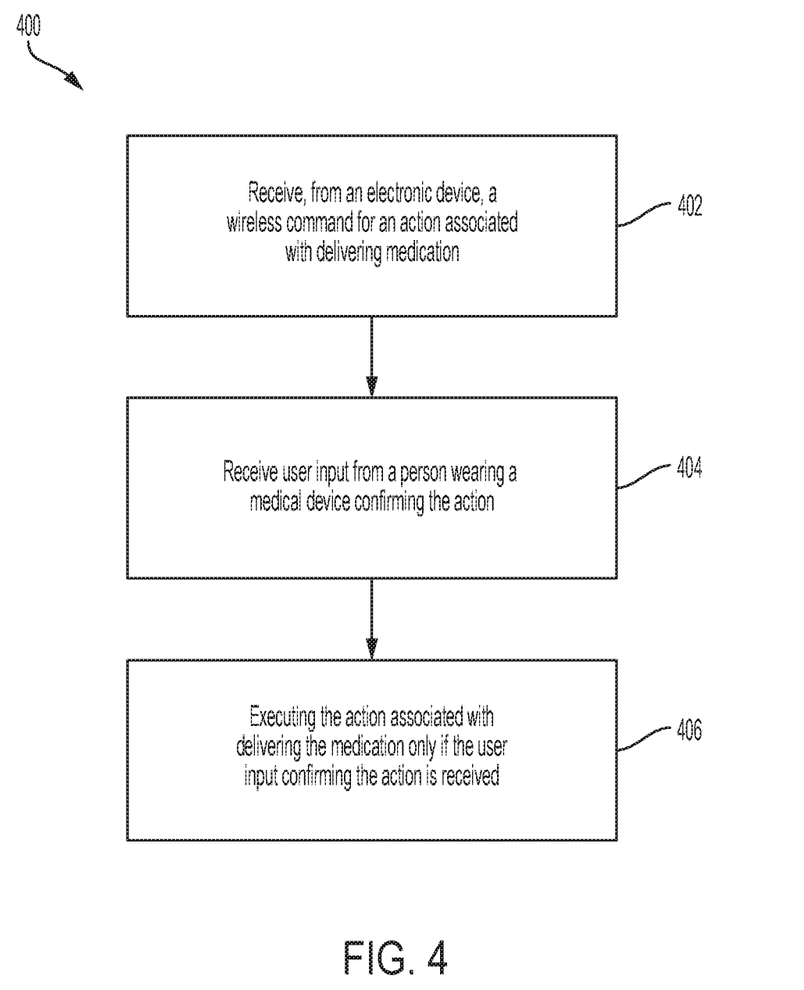
FIG. 4 illustrates a method for dispensing a medication with a wearable drug delivery device.

FIG. 4 illustrates a flowchart 400 of a method for dispensing a medication with a wearable medical device in accordance with the techniques described herein. In a first step 402, a wireless command for an action associated with delivering medication is received from an electronic device. In a second step 404, user input is received from a person wearing the medical device confirming the action. In a third step 406, the action associated with delivering the medication is executed only if the user input confirming the action is received.

The method shown in FIG. 4 can be implemented in various embodiments that require a user to confirm an action prior to any medication dosage being delivered to the user. As an example, the method of FIG. 4 can be implemented when a cellphone 116 is used to determine the dosage to provide to a user (e.g., the cellphone 116 includes a controller that executes an "artificial pancreas" algorithm) and the determined dosage is provided to the wearable insulin pump 102 directly from the cellphone 116 or by way of the electronic device 106 or 202. In various other embodiments described herein, insulin dosages can be provided entirely automatically without patient input.

Figure 5:
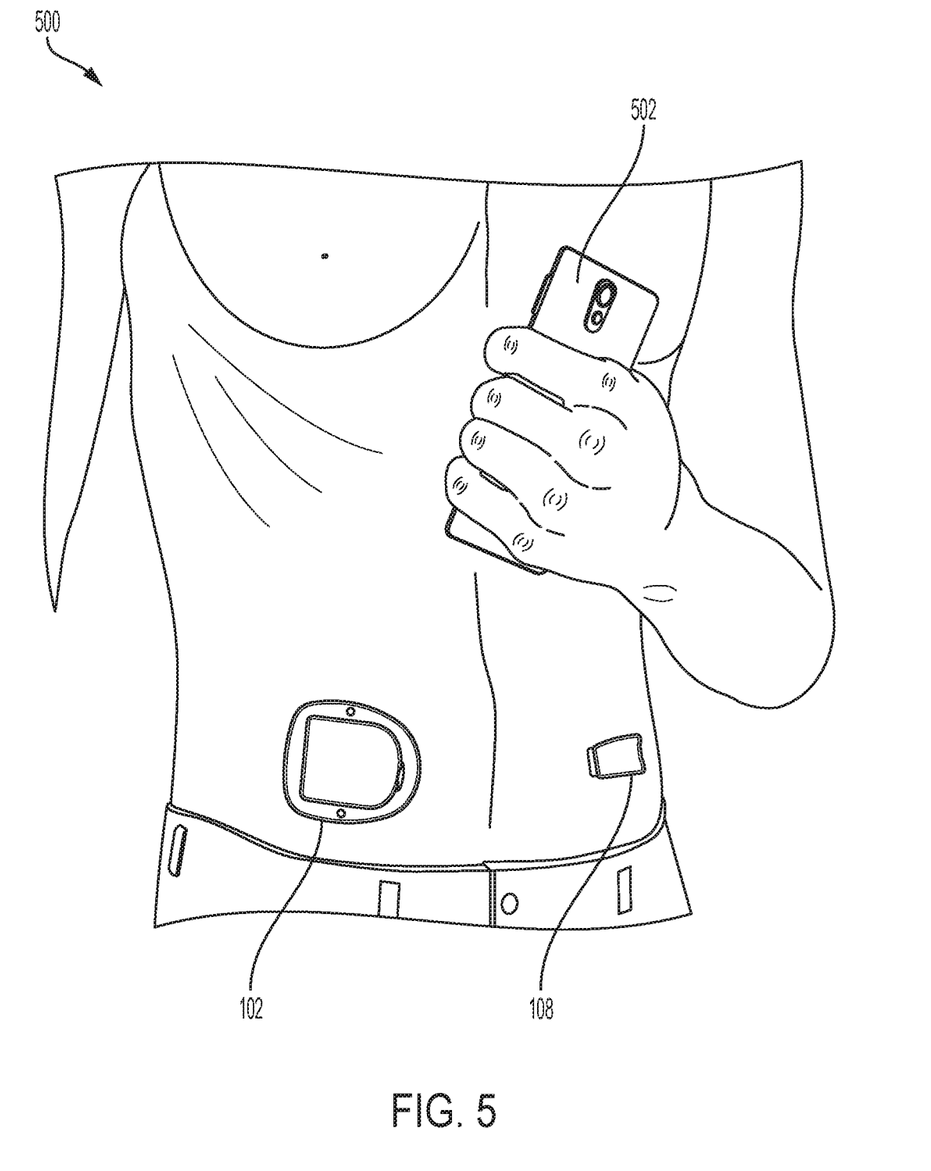
FIG. 5 illustrates a fourth exemplary wearable automated medication delivery system.

FIG. 5 illustrates an exemplary wearable automated medication delivery system 500. The wearable automated medication delivery system 500 can include the wearable insulin delivery device 102, the CGM sensor 108, and a handheld electronic computing device 502. The handheld electronic computing device 502 can be a mobile device or cellphone or can be a dedicated custom electronic device. The wearable insulin delivery device 102 and the CGM sensor 108 can each be directly coupled to a user.

The CGM sensor 108 can provide sensor data to the wearable insulin delivery device 102 and/or the handheld electronic computing device 502. The handheld electronic computing device 502 can include a controller or processor and a memory. The memory can store instructions that can be executed by the controller or processor. The instructions can implement an "artificial pancreas" algorithm when executed. In general, the handheld electronic computing device 502 can include a controller for determining a delivery of insulin to the user (e.g., in terms of dosage amounts and times) based on data from the sensor 108 and providing a corresponding instruction regarding the determined delivery of the insulin to the wearable insulin delivery device 102.

In various embodiments, as mentioned above, the sensor 108 can be provided as part of or embedded within the wearable insulin delivery device 102. Additionally, in various embodiments, as mentioned above, the system 500 can include an intermediate wireless device (e.g., the electronic device 106 or 202) that can relay information wirelessly between the devices depicted in FIG. 5.

In general, the system 500 can automatically monitor glucose levels of the user, automatically determine a delivery of insulin to the user based on the monitored glucose levels, and automatically provide the determined amount of insulin to the user. Each of these steps can be performed without any user input or interaction. In various embodiments, a user confirmation can be required before the insulin is provided to the user as discussed above. For example, when handheld electronic computing device 502 is implemented as a cellphone, for added security, the user can be required to confirm or acknowledge the determined delivery of insulin to the user. Without receiving such confirmation, the delivery can be blocked or prevented. This security feature can mitigate hacking or other cybersecurity risks.

As discussed above, the wearable insulin delivery device 102 can include one or more user output devices that can be used to provide an alarm, alert, notification, or indication to the user that an instruction for insulin delivery has been determined or received. This indication can be audible, visual, and/or vibrational for example. In various embodiments, the indication can include one or more flashing light emitting diodes and/or a vibration provided by the wearable insulin delivery device 102. One or more user input devices provided with the wearable insulin delivery device 102 can be used to provide a required confirmation from the user. The input devices can include a button, a touch screen, or an accelerometer (e.g., such that the input can be a tapping or movement of the wearable insulin delivery device 102). Although user input may be needed to ensure the final step of providing the determined level of insulin to the user occurs, such embodiments can be considered as largely automatic with one or more added security features for the user.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description. Further, many of the techniques and embodiments described are not limited to the delivery of insulin but are applicable to the automated delivery of any medication to a user.

What is claimed is:

1. A wearable automated insulin delivery system, comprising:
    a sensor configured to be coupled to a body of a user, the sensor configured to detect a glucose level of the user, the sensor configured to wirelessly transmit the glucose level of the user;
    a wearable wireless accessory device configured to be coupled to the body of the user separate from the sensor, the wearable wireless accessory device configured to:
        wirelessly receive the glucose level of the user transmitted by the sensor, and wirelessly retransmit the glucose level of the user;
    a cellphone, wherein the cellphone is separate from the wearable accessory device and the sensor, and is configured to:
        wirelessly receive the glucose level of the user retransmitted by the wearable wireless accessory device,
        determine a delivery of insulin to the user based on the glucose level of the user, the determined delivery of insulin to comprise an insulin dosage amount and corresponding delivery time, and
        wirelessly transmit the determined delivery of insulin for delivery to the wearable wireless accessory device,
    wherein the wearable wireless accessory device is configured to wirelessly receive the determined delivery of insulin transmitted by the cellphone and to wirelessly retransmit the determined delivery of insulin; and
    a wearable drug delivery device having a controller, a reservoir of insulin, and an attachable module removably attached to an outer surface of the wearable drug delivery device, the attachable module having a wireless communications interface and a wired connection to the controller and being configured to:
        communicatively couple the wireless communications interface to the controller of the wearable drug delivery device via the wired connection,
        provide wireless communications, via the wireless communications interface, with the wearable wireless accessory device and the cellphone, and wherein the wearable drug delivery device is configured to:
        be directly coupled to the body of the user separate from the wearable wireless accessory device,
        wirelessly receive the determined delivery of insulin retransmitted by the wearable wireless accessory device,
    wherein the controller of wearable drug delivery device is configured to control the wearable drug delivery device to deliver the insulin from the reservoir to the user based on the determined delivery of insulin, and
    wherein the wearable drug delivery device is further configured to receive a confirmation of delivery before the insulin is delivered to the user.

2. The wearable automated insulin delivery system of claim 1, wherein the wearable wireless accessory device includes a user output device, the user output device configured to provide a notification to the user to prompt the user to provide the confirmation of delivery.

3. The wearable automated insulin delivery system of claim 2, wherein the wearable wireless accessory device includes a user input device, the user input device configured to receive the confirmation of delivery from the user.

4. The wearable automated insulin delivery system of claim 3, wherein the insulin is delivered to the user only if the user provides the confirmation within a predetermined amount of time from the provided notification.

5. The wearable automated insulin delivery system of claim 3, wherein the user input device is an accelerometer, the accelerometer configured to detect the confirmation of delivery from the user.

6. The wearable automated insulin delivery system of claim 1, wherein the sensor is positioned within the wearable drug delivery device.

7. A method, comprising:
    detecting glucose levels of a user using a sensor configured to be coupled to the user;
    wirelessly transmitting the detected glucose levels of the user from the sensor to a wearable wireless accessory device;
    wirelessly retransmitting the detected glucose levels of the user from the wearable wireless accessory device to a controller;
    determining, by the controller, a delivery of insulin to the user based on the detected glucose levels of the user received from the wearable wireless accessory device;
    wirelessly transmitting an instruction for the delivery of insulin to the user from the controller to the wearable wireless accessory device;
    wirelessly retransmitting the instruction for the delivery of insulin to the user from the wearable wireless accessory device to a transceiver of an attachable module that is coupled via a removable wired connection to a controller of a wearable insulin delivery device directly coupled to the user;
    providing a notification by the controller of the wearable insulin delivery device via the transceiver of the attachable module to the user indicating receipt of the instruction for the delivery of insulin to the user; and
    delivering the insulin to the user based on a signal from the controller of the wearable insulin delivery device when the user provides a confirmation within a predetermined amount of time from providing the notification, otherwise blocking delivery of the insulin to the user.

8. The method of claim 7, wherein providing the notification comprises providing a visual, audible, or vibrational notification.

9. The method of claim 7, wherein the user provides confirmation using a user input device provided with the wearable wireless accessory device.

10. A wearable automated medication delivery system, comprising:
    a sensor configured to be coupled to a user and to determine a glucose level of a user and to wirelessly transmit the glucose level of the user;
    an electronic device configured to transmit and receive data from a cloud-based server;
    a wearable medical device configured to be coupled adhered via a pad to the user, the wearable medical device including a reservoir and a controller, and
    an attachable module including a transceiver and a wired connection and configured to removably attach to the wearable medical device and communicate with the controller via the wired connection, wherein the transceiver is configured to:
        wirelessly communicate with the sensor and the electronic device via a wireless communication protocol, and
        receive a glucose level directly from the sensor, wherein the controller is configured to:
    determine an insulin bolus size using the received glucose level, and
    control delivery of the determined bolus size to the user.

11. The wearable automated medication delivery system of claim 10, wherein the sensor is embedded within the wearable medical device.

12. The wearable automated medication delivery system of claim 10, wherein: the sensor and the wearable medical device are configured to be coupled to the user at locations on a body of the user separate from one another.

13. The wearable automated medication delivery system of claim 10, further comprising:
    a wearable wireless accessory device including a user input device, wherein the wearable wireless accessory device is configured to:
    present the determined insulin bolus size, and
    receive a confirmation input via the user input device.

14. The wearable automated medication delivery system of claim 10, wherein the determined insulin bolus size includes a medication dosage amount and a corresponding medication delivery time.

15. The wearable automated medication delivery system of claim 10, wherein the controller is configured to wirelessly transmit the glucose level of the user and the determined insulin bolus size to the cloud-based server.

16. The wearable automated medication delivery system of claim 10, wherein the electronic device is a cellphone.

* * * * *

UNITED STATES PATENT AND TRADEMARK OFFICE
CERTIFICATE OF CORRECTION

PATENT NO. : 10,716,896 B2
APPLICATION NO. : 15/359187
DATED : July 21, 2020
INVENTOR(S) : O'Connor et al.

It is certified that error appears in the above-identified patent and that said Letters Patent is hereby corrected as shown below:

In the Claims

Column 12, Claim 10, Line 56; Please remove "coupled"

Signed and Sealed this
Thirteenth Day of October, 2020

Andrei Iancu
*Director of the United States Patent and Trademark Office*